(12) United States Patent
Celentano

(10) Patent No.: US 11,448,674 B2
(45) Date of Patent: Sep. 20, 2022

(54) SYSTEM AND METHOD FOR DETECTION OF CONTACT WITH A TEST STRIP USING CAPACITIVE SENSING

(71) Applicant: Roche Diabetes Care, Inc., Indianapolis, IN (US)

(72) Inventor: Michael J. Celentano, Zionsville, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 558 days.

(21) Appl. No.: 16/592,865

(22) Filed: Oct. 4, 2019

(65) Prior Publication Data

US 2021/0102983 A1 Apr. 8, 2021

(51) Int. Cl.
*G01R 27/26* (2006.01)
*G01N 33/538* (2006.01)
(Continued)

(52) U.S. Cl.
CPC .......... *G01R 27/2605* (2013.01); *G01D 5/24* (2013.01); *G01N 27/3274* (2013.01);
(Continued)

(58) Field of Classification Search
CPC ........ G01R 27/00; G01R 27/02; G01R 27/26; G01R 27/2605; G01N 27/00; G01N 27/26; G01N 27/28; G01N 27/30; G01N 27/327; G01N 27/3271; G01N 27/3273; G01N 27/3274; G01N 33/00; G01N 33/48; G01N 33/50; G01N 33/53; G01N 33/536; G01N 33/537; G01N 33/538; G01N 33/66;
(Continued)

(56) References Cited

U.S. PATENT DOCUMENTS 6,120,676 A * 9/2000 Heller ................ A61B 5/15144
600/584
6,153,069 A * 11/2000 Pottgen .............. G01N 27/3273
435/817

(Continued)

OTHER PUBLICATIONS

Gu, Holly, et al., Capacitive Touch Hardware Design Guide, 2015, Texas Instruments, Design Guide, SLAA576A—May 2013—Revised Nov. 2015; pp. 1-25.

(Continued)

*Primary Examiner* — Hoai-An D. Nguyen

(57) ABSTRACT

An analyte test meter that detects contact between a user and an electrochemical test strip includes a test strip port, a capacitive sensor positioned proximate to the test strip port, and a controller connected to the test strip port and the capacitive sensor. The controller is configured to identify insertion of the electrochemical test strip into the test strip port, apply a drive signal to the capacitive sensor, measure a first response to the drive signal from the capacitive sensor, identify dosing of a fluid sample on the electrochemical test strip, apply the drive signal to the capacitive sensor after the dosing, measure a second response to the drive signal from the capacitive sensor, and detect contact between a body of a user and at least one electrode in the electrochemical test strip in response to a difference between the first and second responses exceeding a predetermined threshold.

19 Claims, 5 Drawing Sheets

(51) Int. Cl.
*G01N 33/66* (2006.01)
*G01N 27/327* (2006.01)
*G01D 5/24* (2006.01)

(52) U.S. Cl.
CPC ........... *G01N 33/538* (2013.01); *G01N 33/66* (2013.01); *G01D 5/2405* (2013.01); *G01R 27/26* (2013.01)

(58) Field of Classification Search
CPC .. G01D 5/00; G01D 5/12; G01D 5/14; G01D 5/24; G01D 5/2405
See application file for complete search history.

(56) References Cited

U.S. PATENT DOCUMENTS

| | | | |
|---|---|---|---|
| 10,948,450 B2* | 3/2021 | Uhegbu | ............ B01L 3/502707 |
| 2002/0055127 A1* | 5/2002 | Gindilis | ................ C12Q 1/001 |
| | | | 435/7.9 |
| 2014/0339100 A1 | 11/2014 | Malecha | |
| 2015/0330937 A1 | 11/2015 | Guthrie et al. | |
| 2016/0299097 A1 | 10/2016 | Lloyd | |

OTHER PUBLICATIONS

Keim, Robert, "Introduction to Capacitive Touch Sensing", Published Nov. 24, 2016 at allaboutcircuits.com, pp. 1-9.
Lion Precision, Tech Note, Nov. 2015, "Capacitive Sensor Operation and Optimizations", LT03-0020, TechNote, pp. 1-13.
Wang, David, 2014, "FDC1004: Basics of Capacitive Sensing and Applications", Texas Instruments, Application Report, SNOA927—Dec. 2014, pp. 1-12.
Keim, Robert, "Circuits and Techniques for Implementing Capacitive Touch Sensing", Published May 30, 2016 at allaboutcircuits. com, 10 pages.
International Search Report and Written Opinion; PCT/US2020/053433; dated Jan. 22, 2021; pp. 9.

* cited by examiner

SYSTEM AND METHOD FOR DETECTION OF CONTACT WITH A TEST STRIP USING CAPACITIVE SENSING

TECHNICAL FIELD

The disclosure relates generally to the field of analyte detection in fluid samples and, more specifically, to systems and methods that detect contact between a user and an electrochemical test strip to improve the accuracy of analyte measurement.

BACKGROUND

Devices, systems, and methods for assaying analytes in body fluids, as well as biosensors for use therein, are well known. For example, electrochemical-based measuring methods are known that generally rely upon correlating a current (amperometry), a potential (potentiometry), or an accumulated charge (coulometry) to an analyte concentration, typically in conjunction with a detection reagent that produces charged-carriers when combined with an analyte of interest. Common types of single-use biosensors include test strips that conduct such electrochemical tests when connected to a meter that generates a series of test signals to analyze reactions that occur between a body fluid sample and one or more reagents that are formed on the test strip.

In general, test strips have a reaction zone that includes measurement electrodes in communication with one or more detection reagents that come into direct contact and thus chemically interact with a body fluid sample. In some amperometric and coulometric electrochemical-based measurement systems, the measurement electrodes are attached to electronic circuitry in an analyte test meter that supplies an electrical potential to the measurement electrodes and measures a response of the test strip to this potential (e.g., current, impedance, charge, etc.). As such, the biosensor is attached or inserted into the analyte test meter, which then measures a reaction between an analyte in the body fluid sample and the detection reagent to determine the analyte concentration, where the measurement of the electrical signal response indicates the analyte concentration.

The analyte measurement process requires a user to place a dose of the fluid sample, which is typically blood but may be a different type of bodily fluid, onto a predetermined region of the test strip that includes the reagent. Ensuring that the proper amount of the fluid is applied to the test strip is one part of the operation of the test strip and analyte test meter, which is sometimes referred to as "sample sufficiency" detection. The sample sufficiency detection ensures that the user has applied enough blood or other bodily fluid to the test strip, but some modern test strips only require a small sample on the order of, for example, 1 µL, or a fraction of a microliter such as a range of 0.9 µL to 0.3 µL to provide a proper sample. In some situations, the user does not retract his or her finger or other body part from the test strip even after the test strip has received a sufficiently large sample to conduct an analyte measurement. The contact between the body of the user and the reagents and electrodes in the test strip may reduce the accuracy of detecting the analyte in the fluid sample. Given these challenges, improvements to analyte test meters that reduce or eliminate the issues produced by contact between a user and the electrochemical test strip during analyte measurement would be beneficial.

SUMMARY

In one embodiment, an analyte test meter includes a test strip port configured to receive a first portion of an electrochemical test strip, a capacitive sensor positioned proximate to the test strip port and coupled to at least one electrode in the electrochemical test strip, and a controller connected to the test strip port and the capacitive sensor. The controller is configured to identify insertion of the first portion of the electrochemical test strip into the test strip port, apply a drive signal to the capacitive sensor after the insertion, measure a first response to the drive signal from the capacitive sensor corresponding to a first level of capacitance in the capacitive sensor, identify dosing of a fluid sample on a second portion of the electrochemical test strip that is outside of the analyte test meter after the measurement of the first response, apply the drive signal to the capacitive sensor after the identification of the dosing, measure a second response to the drive signal from the capacitive sensor corresponding to a second level of capacitance in the capacitive sensor, and detect contact between a body of a user and at least one electrode in the electrochemical test strip in the second portion of the electrochemical test strip in response to a difference between the first response and the second response exceeding a predetermined threshold.

In another embodiment, a method for operating an analyte test meter to detect contact with a user and an electrochemical test strip has been developed. The method includes identifying, with a controller in the analyte test meter, insertion of the first portion of the electrochemical test strip into a test strip port in the analyte test meter, applying, with the controller, a drive signal to a capacitive sensor in the analyte test meter after the insertion, measuring, with the controller, a first response to the drive signal from the capacitive sensor corresponding to a first level of capacitance in the capacitive sensor, identifying, with the controller, dosing of a fluid sample on a second portion of the electrochemical test strip that is outside of the analyte test meter after the measurement of the first response, applying with the controller, the drive signal to the capacitive sensor after the identification of the dosing, measuring, with the controller, a second response to the drive signal from the capacitive sensor corresponding to a second level of capacitance in the capacitive sensor, and detecting, with the controller, contact between a body of a user and at least one electrode in the electrochemical test strip in the second portion of the electrochemical test strip in response to a difference between the first response and the second response exceeding a predetermined threshold.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

DETAILED DESCRIPTION

Figure 1:
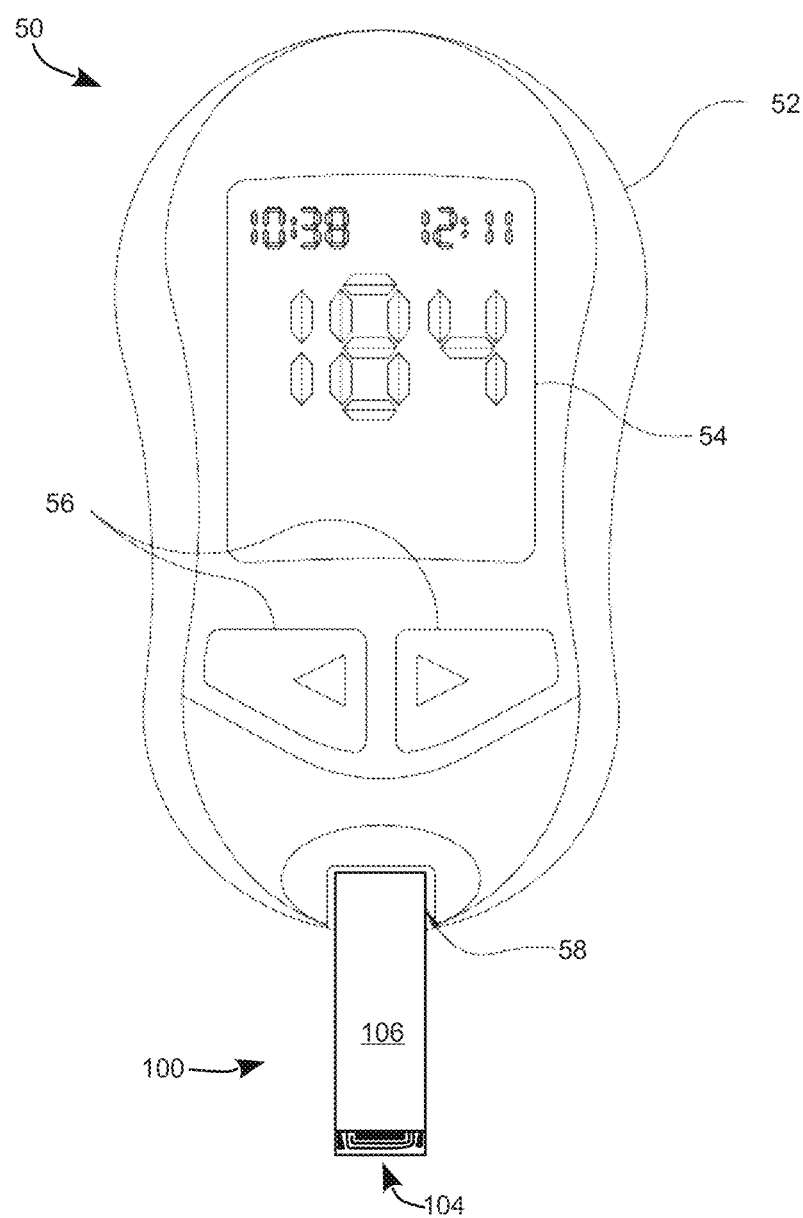
FIG. 1 is an exterior view of one embodiment of an analyte test meter and a test strip that is inserted into a housing of the analyte test meter.

These and other advantages, effects, features and objects are better understood from the following description. In the description, reference is made to the accompanying drawings, which form a part hereof and in which there is shown by way of illustration, not limitation, embodiments of the inventive concept. Corresponding reference numbers indicate corresponding parts throughout the several views of the drawings.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, and features falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, and features useful in solving other problems.

The devices, systems and methods now will be described more fully hereinafter with reference to the accompanying drawings, in which some, but not all embodiments of the inventive concept are shown. Indeed, the devices, systems and methods may be embodied in many different forms and should not be construed as limited to the embodiments set forth herein; rather, these embodiments are provided so that this disclosure will satisfy applicable legal requirements.

Likewise, many modifications and other embodiments of the devices, systems and methods described herein will come to mind to one of skill in the art to which the disclosure pertains having the benefit of the teachings presented in the foregoing descriptions and the associated drawings. Therefore, it is to be understood that the devices, systems and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

The embodiments described herein enable detection of contact between the finger or other body part of a user and exposed electrodes in a portion of a test strip that is located outside of the housing of an analyte test meter. As used herein, the term "contact" with a user refers any of direct contact with the skin of the user and an electrode in the test strip 100 after the electrode has been dosed with a fluid sample, where the contact electrically connects the body of the user to one or more electrodes in the test strip 100. The contact between the user and the exposed electrode occurs via blood or another bodily fluid that provides an electrically conductive path between the electrodes of the test strip and the body of the user. The illustrative examples provided herein often refer to detection of contact of a finger of the analyte meter user with the test strip, but any reference to a finger should be understood to be generally applicable to a body part of a human, including the user of the analyte test meter or any other person handling the analyte test meter.

FIG. 1 depicts an example of an analyte test meter 50 with a removable test strip 100 that is depicted as being inserted into the analyte test meter 50 via a test strip port 58. The test strip 100 is an electrochemical test strip that includes both a chemical reagent that reacts with a fluid sample and electrodes that enable the analyte test meter 50 to apply electrical signals to the reagent and to detect response signals from the reagent to detect levels of one or more analytes in the fluid sample. All references to a "test strip" herein refer to an electrochemical test strip such as the test strip 100 or other suitable electrochemical test strip configuration.

The analyte test meter 50 of FIG. 1 is further embodied as a blood glucose meter that detects and displays a level of glucose in a blood sample that is applied to the test strip 100 for illustrative purposes. The analyte test meter 50 includes at least one output device, which is depicted as the display device 54 in FIG. 1, and at least one input device, which is depicted as the control buttons 56 in FIG. 1. Additional examples of output devices include indicator lights, audio alarms or synthesized speech audio outputs, haptic feedback devices, and the like. Additional examples of input devices include touchscreen input devices, speech recognition devices, keypads, and the like. While the analyte test meter 50 of FIG. 1 measures a glucose analyte in a blood sample, the embodiments described herein are not limited to blood glucose meters since the embodiments described herein are suitable for use in analyte test meters that measure different types of analytes contained in blood or other bodily fluid samples. Examples of other analytes include, but are not limited to, alcohols, amino acids, 1,5-anhydroglucitol, cholesterols, fructosamine, glycerines, HbA1c, HDL 10 ketones/ketone bodies, lactates, lactate dehydrogenase, malates, pyruvates, sorbitol, creatinine, triglycerides, and uric acid.

The test strip 100 is formed from an electrically non-conductive base layer, electrodes formed on the non-conductive base layer, and a non-conductive spacer layer 108 that covers a portion of the electrodes leaving exposed electrodes at both ends of the test strip 100. In some test strip embodiments, a separate non-conductive cover layer (shown in FIG. 3) is placed over the spacer layer to form a fluid chamber over the reagent that is formed on the second portion 104 of the test strip 100, although in other embodiments the reagent is left exposed. Examples of electrodes include, but are not limited to, one or more working electrodes, reference electrodes, counter electrodes, and sample-sufficiency electrodes. The electrodes extend along the length of the test strip 100 from a first portion of the test strip (not shown in FIG. 1) that includes electrode contacts that are electrically connected to components in the analyte test meter 50 via electrical contacts contained in the test strip port 58 to a second portion of the test strip 104 that is located outside of the analyte test meter 50. The second portion of the test strip 104 includes the exposed electrodes and at least one reagent that is applied to the electrodes. The second portion 104 of the test strip 100 receives a fluid sample and the analyte test meter 50 applies electrical signals to the electrodes via the connection in the test strip port 58 for the measurement of an analyte that is present in the sample and that produces a chemical reaction in the reagent. The exposed second portion 104 is also referred to as a sample chamber since this portion of the tests strip 100 receives the sample of the fluid that contains the analyte. Alternative embodiments of test strips include different arrangements of layers and electrode configurations that provide electrical connections between one or more reagents that receive a fluid sample and an analyte test meter.

Figure 2:
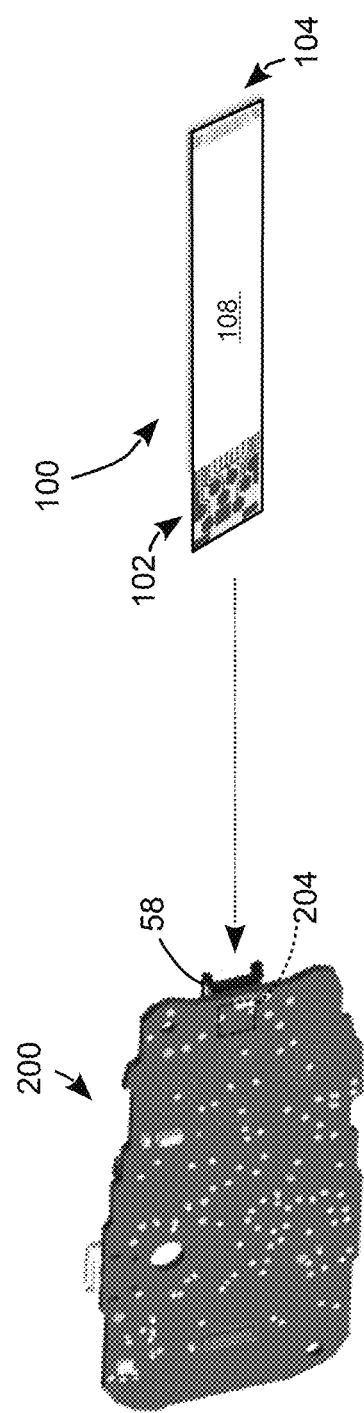
FIG. 2 is a diagram of a printed circuit board, capacitive sensor, and test strip port in the analyte test meter of FIG. 1 that receives a test strip.

FIG. 2 is a depiction of selected components that are contained within the housing 52 of the analyte test meter 50. FIG. 2 depicts a printed circuit board (PCB) 200, the test strip port 58, and a capacitive sensor 204 that is formed in the PCB 200 and contained within the housing 52 of the analyte test meter 50. While not shown in greater detail, the PCB 200 also provides electrical connections to the controller, batteries, and other electronic components in the blood glucose meter 50. FIG. 2 also depicts the test strip 100 removed from the test strip port 58 to depict the first portion 102 at one end of the test strip 100 that includes the exposed electrode terminals that enable electrical connection of the test strip 100 to the analyte test meter 50 when the first portion 102 is inserted into the test strip port 58. As depicted in FIG. 2, the capacitive sensor 204 is located proximate to the test strip port 58 and to the electrodes in the test strip 100 when the first portion 102 of the test strip 100 is inserted into the test strip port 58. In the embodiment of FIG. 2, the capacitive sensor 204 is integrated into the PCB 200, although in other embodiments the capacitive sensor 204 can be a separate component instead of being integrated into the PCB 200.

Figure 3:
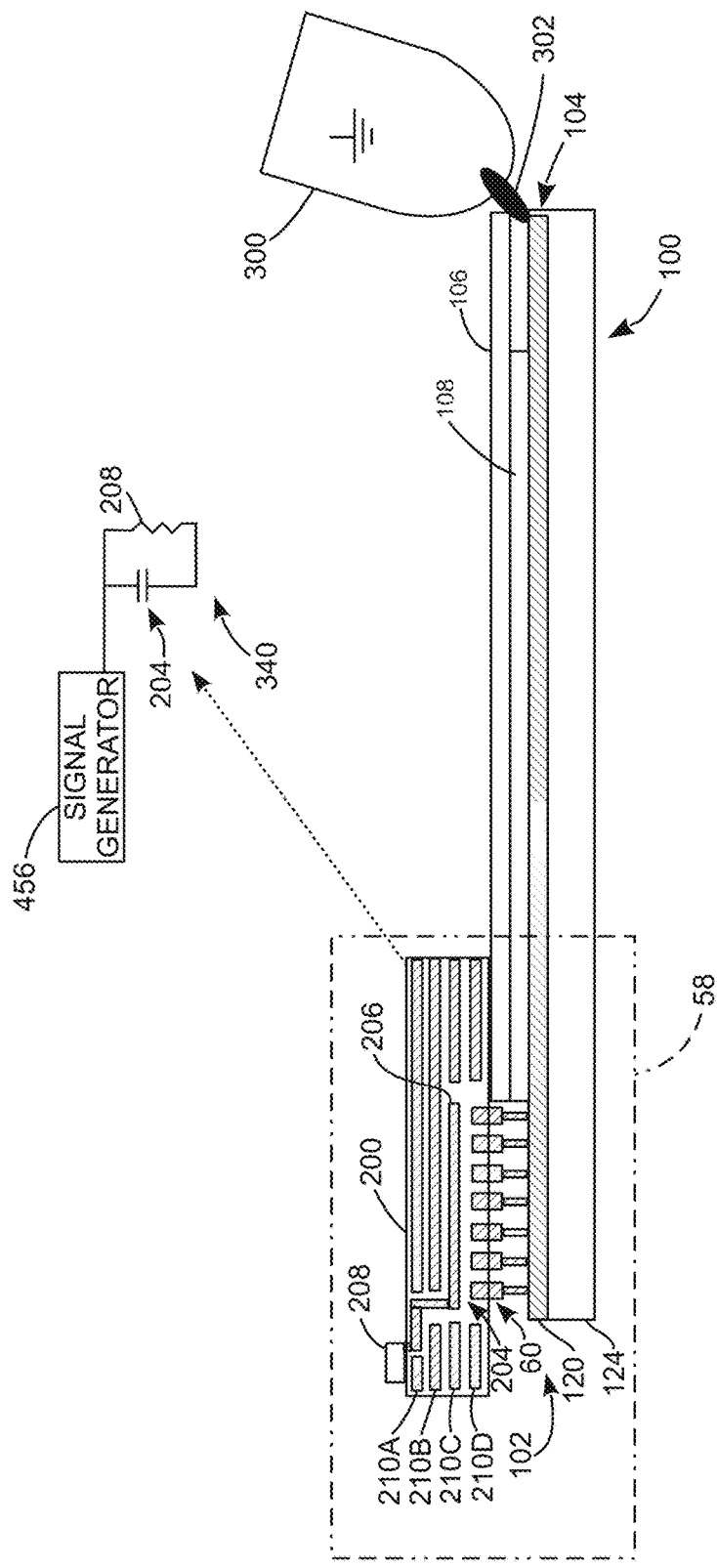
FIG. 3 is a simplified profile view of a capacitive sensor positioned within a housing of the analyte test meter of FIG. 1 in proximity to electrodes of a test strip that is inserted into the analyte test meter.

FIG. 3 depicts additional aspects of the arrangement of the capacitive sensor 204 in the analyte test meter 50 and the test strip 100 including a portion of the PCB 200 and the test strip port 58. FIG. 3 depicts layers of the test strip 100 including a non-conductive base layer 124 that is formed from plastic or another non-conductive material, the electrodes 120 in the test strip 100, the non-conductive spacer layer 108, and the non-conductive cover 106 that protects the electrodes outside of the exposed first portion 102 that connects the electrodes to the test strip port 58 and the second portion 104 that bears the reagent. In FIG. 3, the cover layer 106 overhangs the spacer layer 108 to form a fluid chamber that receives a blood sample from a finger 300 of the user, although alternative test strip configurations receive other types of fluid samples. Additionally, in some test strip embodiments a cover layer does not overhang the second portion 104 of the test strip, such as the test strip embodiment depicted in FIG. 1, which leaves the second portion of the test strip exposed to receive the fluid sample.

FIG. 3 depicts the capacitive sensor 204 with a capacitor that is formed by a first conductive plate 206, which is formed as a planar conductor in a layer of copper or other electrically conductive material in the PCB 200, and a second conductive plate that is formed by the electrical contacts 60 in the test strip port 58 that are configured to establish electrical connections between the electrodes 120 in the test strip 100 and to a controller and other components in the analyte test meter 50. The conductive plate 206 is, for example, a copper pad or a pad formed from another conductor with a square, rectangular, circular, or other planar shape that acts as a plate in a capacitor. The two plates 206 and 60 are formed in a substantially parallel orientation with a predetermined separation in the PCB 200. The PCB 200 provides an electrical insulative layer that forms a dielectric between the conductive plate 206 and the contacts 60. In the embodiment of FIG. 3, the thickness of the dielectric is on the order of 0.05 mm to 1.0 mm, although smaller or larger dielectric thicknesses can be used in different configurations based on the designed capacitance level and the relative permittivity of the dielectric material. While FIG. 3 depicts a dielectric formed by one or more layers in the PCB, in alternative configurations one or more dielectric materials including air gaps or other non-conductive materials such as glass or a ceramic, and combinations thereof, form the dielectric.

The PCB 200 includes additional conductive layers, such as the conductive layers 210A-210D in the illustrative example of FIG. 3, which are arranged to minimize interference with the capacitive sensor 204. For example, the conductive layer 210D includes an aperture to ensure that no conductive elements are interposed in the dielectric between the conductive plate 206 and the electrical contacts 60. The conductive plate 206 is formed from a portion of the conductive layer 210C, and a gap around the conductive plate 206 isolates the layer 210C from the conductive plate 206 to enable capacitive coupling with the electrical contacts 60. Of course, those if skill in the art will note that the presence of multiple conductive layers in the PCB 200 produces parasitic capacitances. However, the configuration of the capacitive sensor 204 reduces the effects of these parasitic capacitances and, as described below, the operation of the capacitive sensor 204 in the analyte test meter 50 relies on relative changes in capacitance levels, which reduce or eliminate the influence of parasitic capacitances during the detection of user contact with the test strip 100.

In the embodiment of FIG. 3, the capacitive sensor 204 is connected to a resistor 208, and the capacitive sensor 204 and resistor 208 form a resistor-capacitor (RC) circuit that is depicted schematically as RC circuit 340 in FIG. 3. The resistor 208 is electrically connected to the conductive plate 206 by a set of vias that are depicted in FIG. 3 and to at least one of the electrical contacts 60 in the PCB 200 via electrical traces in the PCB 200 (not shown) that also connect the electrical contacts 60 to the controller 450. For example, in one configuration one or more of the contacts 60 that are configured to be electrically connected to the counter electrode in the test strip 100 form the second plate in the capacitive sensor 204 and these contacts are connected to the resistor 208. The resistor 208 is depicted as a surface-mount resistor with a resistance of 1 MΩ for illustrative purposes, but other resistor configurations with a higher or lower resistance are used in different embodiments. Additionally, FIG. 3 depicts the resistor 208 in close proximity to the conductive plate 206 and the electrical contacts 60 for illustrative purposes, but the resistor 208 can be placed in a different location of the PCB. The RC circuit 340 is electrically connected to a signal generator 456 within the analyte test meter 50 that is described in further detail below.

During operation of the analyte test meter 50, the electrodes 120 in the test strip 100 are inserted into the test strip port 58, which enables the electrodes 120 to increase the effective size of the electrical contacts 60 that form one of the conductive plates in the capacitive sensor 204. Because the electrodes 120 extend outside of the housing 52 of the analyte test meter 50 and come into contact with the body of the user 300, the capacitive sensor 204 that is located within the analyte test meter 50 can detect contact between the user and the second portion of the test strip 104 that is located outside of the housing 52 of the analyte test meter 50. As depicted in FIG. 3, the body of the user 300 acts as an electrical ground when placed in contact with the electrodes 120 via a blood sample 302 or other fluid sample. When in contact with the electrodes 120, the electrical ground increases the effective capacitance of the capacitive sensor 204. As described in further detail below, a controller in the analyte test meter 50 identifies the relative difference between the capacitance level in the capacitive sensor 204 prior to when the test strip 100 receives the dose of the fluid sample and the larger capacitance level that occurs when then user 300 contacts the test strip 100 after dosing to detect the contact.

Figure 4:
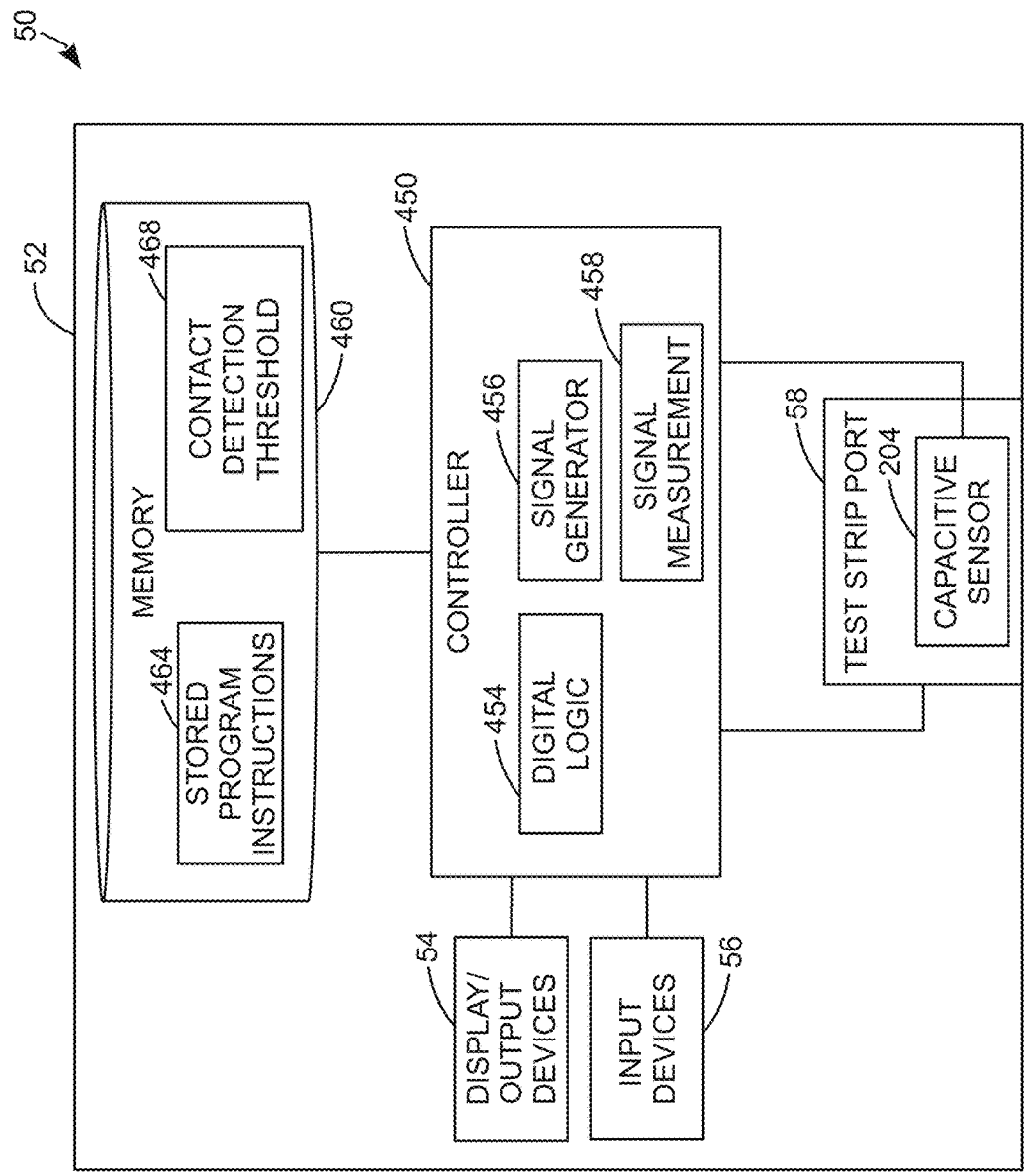
FIG. 4 is a schematic diagram of components in an analyte test meter that enable sensing of contact between a finger or other body part of a user and a test strip that is inserted into the analyte test meter.

FIG. 4 is a schematic diagram that depicts additional components of the analyte test meter 50. The analyte test meter 50 includes a controller 450 that is operatively connected to the test strip port 58, the capacitive sensor 204, the display or other output devices 54, and the input devices 56. The controller 450 includes one or more digital logic devices 454 such as a microcontroller, microprocessor, application specific integrated circuit (ASIC), or any other electronic device or devices that implement the digital logic functions to perform the operations to detect contact between a user and a test strip that is inserted in the test strip port 58 and to perform the analyte measurement process. While not depicted in greater detail, the controller 450 also includes input/output (I/O) hardware that operatively connects the controller 450 to the display and output devices 54, the input devices 56, and the memory 460.

The controller 450 further incorporates one or more signal generators 456 that generate a drive signal for the capacitive sensor 204 and that generate alternating current (AC), direct current (DC), or sequences of AC and DC signals that are applied to electrodes in a test strip via the test strip port 58 to perform an analyte measurement process. The signal generators 456 include, for example, oscillators, modulators, amplifiers, and other circuits that generate DC and AC output signals with controlled output amplitudes, duty cycles, frequencies, and waveforms. The controller 450 further incorporates one or more signal measurement devices 458 including, for example, digital and analog filters, amplifiers, voltage and current sensors, analog-to-digital converters that convert an analog response signal to digital data for processing by the digital logic devices in the controller 450, and any other suitable signal measurement components. For illustrative purposes, the signal generators 456 and the signal measurement devices 458 refer to separate signal generators and signal measurement devices that are connected to the capacitive sensor 204 and to signal generators and signal measurement devices that are connected to the electrodes in the test strip 100 via the electrical contacts 60 in the test strip port 58. In one embodiment, the signal generators 456 and the signal measurement devices 458 that are connected to the capacitive sensor 204 are specifically configured as touch sensors that, in the embodiments described herein, detect contact between the user and the exposed portion of the test strip 100 that is outside of the housing 52 of the analyte test meter 50. A separate signal generator 456 and signal measurement device 458 combination that is connected to the electrical contacts 60 in the test strip port 58 generates the signals and measures signal responses for analyte detection in the test strip 100.

As described in further detail below, the controller 450 detects contact between the user and the test strip 100 prior to measuring the concentration of the analyte in the fluid sample on the test strip 100. However, in an alternative configuration a single signal generator and signal measurement device can implement the functions described herein in two different operating modes that detect contact between the test strip and the user and that perform the analyte test sequence after detecting that the user is not in contact with the test strip. While FIG. 4 depicts the controller 450 as one device, such as a System-on-a-Chip (SoC), for illustrative purposes, in other embodiments the controller 450 includes multiple digital and analog devices that are connected to each other to implement the controller 450.

The memory 460 includes, for example, one or more non-volatile and volatile digital data storage devices. The memory 460 holds stored program instructions 464 that the controller 450 executes to implement the functions described herein. The memory 460 further stores a threshold 468 that corresponds, either directly or indirectly, to a change in capacitance level in the capacitive sensor 204, which enables the controller 450 to determine if the user is in contact with one or more electrodes in a test strip. In one embodiment, the threshold 468 is a time threshold that the controller 450 uses to detect contact with the user based on a change in the amount of time required for the voltage of the capacitive sensor 204 in the RC circuit 340 to discharge to a predetermined threshold level, where this discharge time is affected by the capacitance level. While not depicted in greater detail herein, the memory 460 also stores any other data used for the operation of the analyte test meter 50 including, but not limited to, a history of analyte test results, fixed parameter values used in the analyte measurement process, and personalized user setting parameters.

Figure 5:
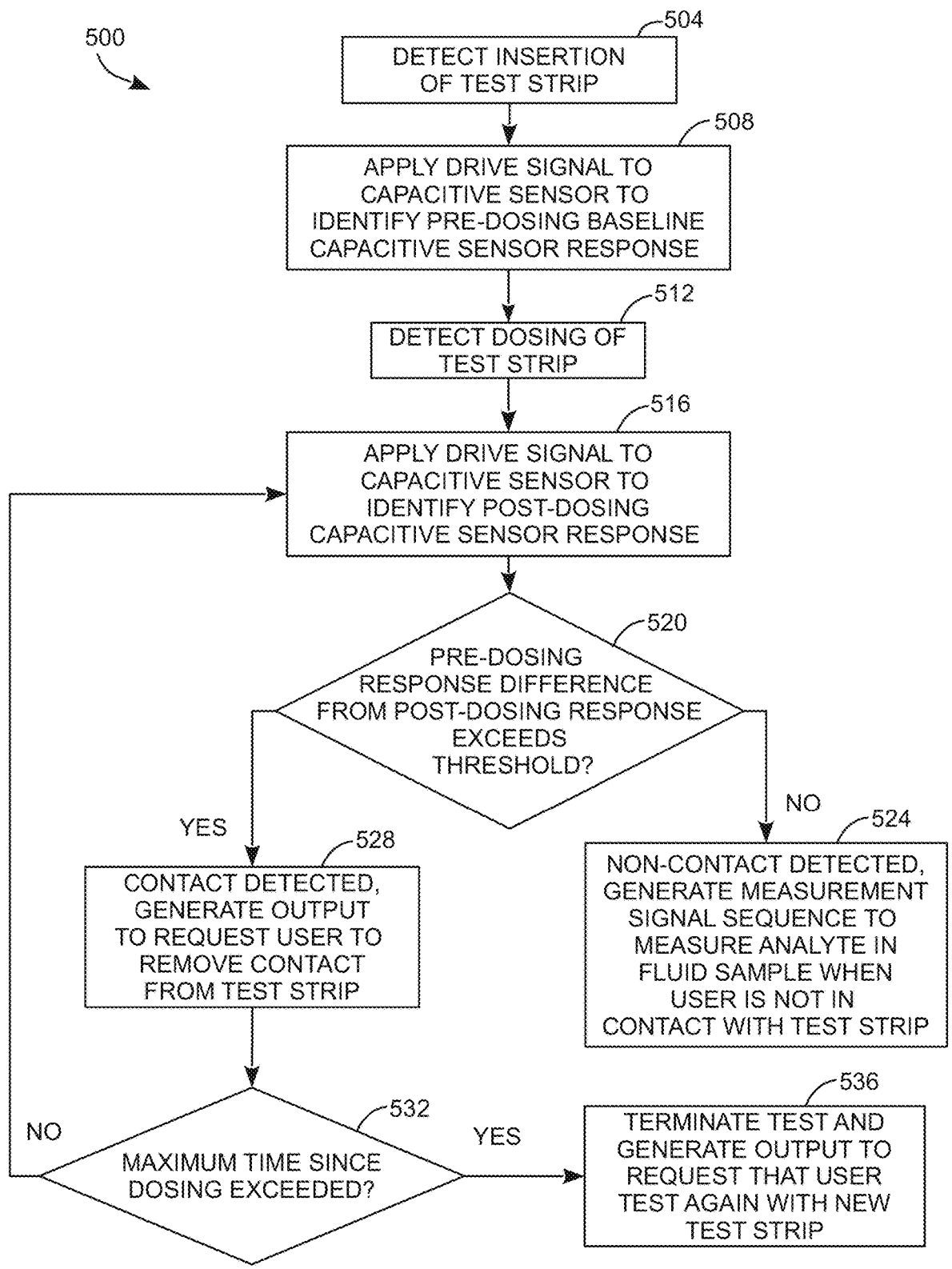
FIG. 5 is a block diagram of a process for detection of contact between a finger or other body part of a user and a test strip.

FIG. 5 is a block diagram of a process 500 for operation of an analyte test meter that detects contact between a finger or other body part of a user and electrodes in a portion of a test strip that is located outside of the analyte test meter. In the description below, a reference to the process 500 performing a function or action refers to the operation of a controller to execute stored program instructions to perform the action in association with components in an analyte test meter. The process 500 is described in conjunction with the analyte test meter 50 and the foregoing embodiments for illustrative purposes.

The process 500 begins as the controller 450 detects the insertion of a test strip in the test strip port 58 (block 504). In one embodiment, the controller 450 detects the insertion of the first portion 102 of the test strip 100 into the test strip port 58 based on an electrical continuity test through a circuit that a conductor in the test strip 100 closes upon insertion in the test strip port 58 or via any other suitable sensor that detects insertion of the test strip 100. Upon initial insertion, the test strip 100 has not received a dose of the fluid sample.

The process 500 continues as the controller 450 applies a first drive signal to the capacitive sensor 204 to identify a baseline capacitance level in the capacitive sensor prior to dosing of the test strip 100 (block 508). The controller 450 activates the signal generator 456 to apply a drive signal to the capacitive sensor 204 and measures a discharge time of the capacitor formed in the RC circuit 340. In the analyte test meter 50, the controller 450 operates the signal generator 456 to apply a pulsed DC drive signal to the capacitive sensor 204, which charges the capacitor that is formed by the conductive plate 206 in the capacitive sensor 204 and the electrodes in the test strip 100. The pulsed DC drive signal is, for example, a digital logic output signal that is generated at a predetermined voltage level (e.g. 3.3V or 5V although other embodiments use different voltage levels) or another DC output signal that is generated for a predetermined period of time to charge the capacitor in the RC circuit 340 to a sufficiently high level to enable measurement of the amount of time that the RC circuit takes to discharge to a low-voltage threshold level. In one embodiment, the controller 450 applies the pulsed DC drive signal for a length of time that charges the capacitor to nearly the same voltage level as the DC signal, although the capacitor may be charged to a somewhat lower predetermined voltage level as well. After applying the pulsed DC drive signal for a predetermined time period, the controller 450 deactivates the signal from the signal generator 456 and uses a voltage sensor or other signal measurement device 458 to monitor the discharge of the voltage as the RC circuit 340 discharges over time. In one embodiment, the controller 450 starts a timer, such as an incrementable counter or another suitable timer, upon deactivation of the pulsed DC drive signal. The timer runs until a voltage sensor 458 detects that the measured voltage level of the RC circuit 340 has discharged to a predetermined low-voltage threshold (e.g. 0.60 V although other embodiments use different low-voltage levels). The elapsed time that the RC circuit 340 takes to discharge indicates the level of the capacitance of the capacitor as described in further detail below.

The time taken for the measured voltage from the RC circuit 340 to discharge to a reference voltage level provides a baseline capacitive sensor response for the capacitive sensor 204 prior to dosing of the test strip 100 while the electrical contacts 60 are connected to the electrodes 120 in the test strip 100. The time required for the capacitive sensor 204 to charge and discharge is related to the RC time constant: $\tau = RC$ where R is a resistance in Ohms and C is the capacitance in Farads. In the embodiments described herein, R has a predetermined value of the resistor 208 (e.g. 1 M$\Omega$) and C is the capacitance of the capacitive sensor (e.g. 200 picoFarads (pF)), although the values presented herein are non-limiting and, as described below, the embodiments described herein can accommodate RC circuits that have varying R and C values. The precise capacitance level of the capacitive sensor 204 may vary somewhat from a nominal value due to environmental factors such as temperature and humidity, and the controller 450 measures a first response from the capacitive sensor that corresponds to the capacitance level prior to dosing as a baseline measurement to ensure accurate detection of contact with the user 300 during the process 500. The duration of each pulse in the pulsed DC drive signal varies based on the configuration of the RC circuit, but in one illustrative embodiment the pulse duration is 1 millisecond, which charges an RC circuit with a 1 M$\Omega$ resistor and a 200 pF capacitor to approximately 99% of maximum charge where $\tau = (1\ M\Omega)(200\ pF) = 2*10^{-4}$ sec and 1 millisecond represents five of the time constant periods $\tau$. The nominal 1 M$\Omega$, and 200 pF values provided above are not necessarily precise values of the capacitor and resistor in this illustrative embodiment of the RC circuit 340 since these values may vary during operation, but are estimates that are sufficiently accurate to ensure that the capacitive sensor 204 charges to approximately full capacity. Upon deactivation of the signal, the capacitive sensor 204 discharges through the resistor 208 at substantially the same rate as the charge rate, and in this example the capacitor discharges to a charge level of approximately 1% after 1 millisecond. As is known to the art, the time constant $\tau$ indicates the amount of time taken for the capacitor in the RC circuit to charge to $1-e^{-1}$ of the total capacity of the capacitor (approximately 63.2%) or to discharge to $e^{-1}$ of the total capacity of the capacitor (approximately 36.8%). The capacitor charge and discharge times follow an exponential curve, and the capacitor asymptotically approaches maximum or minimum charge over additional time periods. The signal measurement circuits 458 measure the voltage level of the capacitive sensor 204 during the discharge process, and the controller 450 measures the amount of time required for the capacitor to discharge to the predetermined low voltage level. The measured discharge time corresponds to the capacitance level of the capacitive sensor 204 since the measured discharge time is related to the capacitance level of the capacitive sensor 204 with longer times indicating larger capacitances and shorter times indicating smaller capacitances.

The process 500 continues as the controller 450 detects the dosing of the test strip with the fluid sample (block 512). In the analyte test meter 50, the controller 450 detects the application of the fluid sample to the second portion 104 of the test strip 100 by generating a detection signal through two sample sufficiency electrodes that are exposed to the fluid sample. A sufficiently large fluid sample applied to the second portion 104 of the test strip 100 establishes a reduced-impedance electrical connection between the sample sufficiency electrodes, and the controller 450 identifies that the test strip 100 has received a fluid sample of sufficient size to conduct the analyte measurement process.

The process 500 continues as the controller 450 applies the drive signal to the capacitive sensor 204 to identify the capacitance level in the capacitive sensor after detecting that the test strip 100 has received a dose of the fluid sample (block 516). In the analyte test meter 50, the controller 450 generates the same drive signal both before and after detecting dosing of the test strip 100. The controller 450 measures the discharge time for the capacitive sensor 204 to discharge to the predetermined voltage level in the same manner as described above to measure a second response to the drive signal from the capacitive sensor corresponding to the second level of capacitance in the capacitive sensor after the dosing has occurred. In at least some instances, the addition of the fluid sample to the electrodes in the second portion of the test strip 100 increases the capacitance level of capacitive sensor 204. However, this contribution to the capacitance is substantially smaller in magnitude than the increase in capacitance that occurs in response to contact between the user 300 with the electrodes 120 in the test strip 100 after the blood or other fluid sample is applied to the test strip to establish an electrical connection between the body of the user 300 and the capacitive sensor 204 via the test strip electrodes 120 and the contacts 60 in the test strip port 58. As described above, the body of the user 300 effectively acts as an electrical ground that increases the capacitance level of the capacitive sensor, and consequently increases the discharge time of the capacitive sensor in response to the drive signal relative to the baseline discharge time that is measured prior to dosing the test strip 100.

During process 500, the controller 450 identifies a difference between the pre-dosing and post-doing signal responses from the capacitive sensor 204 to detect user contact with the test strip 100 after dosing if the differences exceed a predetermined threshold (block 520). In the embodiment of FIG. 5, the contact detection threshold data 468 in the memory 460 corresponds to a maximum time delta from the pre-dosing discharge time that the controller 450 uses to identify contact with the user 300 if the contact detection threshold time is exceeded. For example, if the maximum time delta is $2 \times 10^{-4}$ sec and the pre-dosing measured signal response from the capacitive sensor 204 indicates a discharge time of $4 \times 10^{-4}$ sec, then a post-dosing signal response discharge time of $5 \times 10^{-4}$ sec lies within the maximum time threshold ($4 \times 10^{-4}$ sec+$2 \times 10^{-4}$ sec), which indicates that the user 300 is not in contact with the test strip 100. However, if the discharge time exceeds the predetermined threshold 468, such as a post-dosing discharge time of $8 \times 10^{-4}$ sec, then controller 450 detects that the user 300 is in contact with the test strip 100. The controller 450 optionally performs a series of signal response measurements and averages the measurement values to identify if the signal response exceeds the predetermined threshold to reduce or eliminate the effects of transient noise in the capacitive sensor 204. As described above, some changes in the signal response from the capacitive sensor 204 after the test strip receives the fluid dose may occur, and the controller 450 uses the contact detection threshold 468 to distinguish between a smaller change in capacitance that occurs due to receiving the fluid sample compared to the larger change in capacitance that occurs due to contact with the user 300. In another embodiment, the threshold 468 represents a percentage of the pre-dosing discharge time, such as a threshold of 50% of the measured pre-dosing discharge time in the signal response from the capacitive sensor 204. As described above, during the process 500 the controller 450 detects contact or non-contact with the user 300 based on relative changes in the measured signal response from the capacitive sensor 204 in the RC circuit 340 in the pre-dosing baseline state and post-dosing of the test strip 100. As such, the precise values of the capacitor in the capacitive sensor 204 and the resistor 208 may vary both over time in a single analyte test meter 50 and between different analyte test meters 50 while the analyte test meter 50 provides accurate contact detection by measuring the relative changes in capacitance instead of the precise absolute capacitance and resistance values of the capacitive sensor 204 and the resistor 208, respectively.

If the controller 450 measures that the difference between the first response to the drive signal prior to dosing the test strip 100 and the second response to the drive signal after dosing the test strip 100 does not exceed the predetermined threshold (i.e. the difference between the first response and the second response is less than the predetermined threshold) (block 520), then the controller 450 identifies that the user 300 is not in contact with the test strip 100 (non-contact) and the analyte test meter 50 generates an measurement signal sequence to identify the level of analyte in the fluid sample that is applied to the test strip 100 (block 524). In one embodiment where the analyte test meter is a blood glucose meter, the controller 450 operates the signal generator 456 to apply a test sequence including a series of AC, DC, or AC and DC voltage signals to the electrodes 120 in the test strip 100 via the contacts 60 in the test strip port 58. The signal measurement device 458 in the controller 450 detects responses to the test sequence signals, typically in the form of electrical current responses, and the controller 450 measures the analyte level based on the responses to the test sequence signals. The measurement of analytes in electrochemical test strips is generally known to the art and is not described in further detail herein. In some embodiments, the controller 450 also deactivates the pulsed DC signal used for contact detection with the user 300 prior to initiating the test sequence to measure the analyte.

If the controller 450 measures that the difference between the first response to the drive signal prior to dosing the test strip 100 and the second response to the drive signal after dosing the test strip 100 exceeds the predetermined threshold (block 520), then the controller 450 identifies that the user 300 is in contact with the test strip 100 and the analyte test meter 50 generates an output to request that the user 300 withdraw from contact with the test strip 100 (block 528). Using the analyte test meter 50 as an example, the controller 450 operates the display device 54 to produce an output message including text, graphics, or both text and graphics to request that the user remove a finger or other body part from contact with the second portion 104 of the test strip 100. In other configurations, the controller 450 operates an indicator light, generates an audible output using a speaker, or operates a haptic feedback device to produce an output request for the user to remove contact from the test strip 100. In one embodiment, the controller 450 incorporates a short delay (e.g. 1-2 seconds) from the dose detection until generating the output message to provide the user 300 time to withdraw the finger from the test strip 100 before generating the request message.

During the process 500 the controller 450 continuously detects the contact with the user 300 as described above with reference to the processing of blocks 516, 520, and 528 until the user 300 either releases contact to enable measurement of the analyte level as described above with reference to block 524, or the process 500 exceeds a maximum contact time threshold that has elapsed since detecting the dosing of the test strip 100 (block 532). If the user 300 does not release contact with the test strip 100 before exceeding the maximum time from dosing, then the controller 450 terminates the process 500 without measuring the analyte level and generates an output request, using the display device 54 or other suitable output device, for the user to remove the test strip 100 and to test again with a different test strip (block 536). The controller 450 terminates the process 500 after maximum time threshold is reached to avoid measurement errors that may occur when a fluid sample remains on the test strip 100 for a sufficiently long period that evaporation of the fluid occurs, which can reduce the accuracy of the analyte measurement. In one embodiment the maximum time period threshold is 10 seconds, but the maximum time threshold may vary based on the configuration of the test strip 100.

The specific configuration of the capacitive sensor 204 and operation in the analyte test meter 50 described above is provided for illustrative purposes, and other capacitive sensor configurations are also suitable for use in the analyte test meter 50. For example, a mutual capacitive sensor that employs mutual capacitance includes capacitors that are formed in the capacitive sensor itself in the same location as the conductive plate 206 depicted above. In this embodiment, the contacts 60 in the test port 58 and the electrodes 120 in the test strip 100 are not directly part of the capacitive sensor, but these elements still affect the mutual capacitance between these capacitors within the capacitive sensor. The contact between the user and the electrodes in the test strip 100 further changes the mutual capacitance levels in the capacitive sensor, which the controller 450 detects to identify that the user is in contact with the electrodes in the second portion 104 of the test strip 100. Additionally, while the embodiments described herein measure changes in capacitance indirectly based on the measured time for discharge of an RC circuit, other embodiments that measure the capacitance of one or more capacitors indirectly or directly to detect contact with the user are also suitable for use in the analyte test meter 50 and other analyte test meter embodiments. More generally, the analyte test meter 50 employs a capacitive sensor that incorporates or is capacitively coupled to the electrodes 120 in the test strip 100 to detect a change in capacitance that occurs in response to contact with the finger or other body part of a user.

As described above, the embodiments described herein enable an analyte test meter to detect contact between the body of the user and one or more electrodes in a biochemical test strip that are located outside of the analyte test meter. The detection of user contact with the electrodes in the test strip enables the analyte test meter to avoid the generation of a test sequence for measurement of the analyte while the user is in contact with the electrodes in the test strip, which reduces the likelihood of interference with the analyte measurement process to improve the accuracy of the analyte detection meter.

This disclosure is described in connection with what are considered to be the most practical and preferred embodiments. However, these embodiments are presented by way of illustration and is not intended to be limited to the disclosed embodiments. Accordingly, one of skill in the art will realize that this disclosure encompasses all modifications and alternative arrangements within the spirit and scope of the disclosure and as set forth in the following claims.

What is claimed is:

1. An analyte test meter comprising:
a test strip port configured to receive a first portion of an electrochemical test strip;
a capacitive sensor positioned proximate to the test strip port and coupled to at least one electrode in the electrochemical test strip; and
a controller connected to the test strip port and the capacitive sensor, the controller being configured to:
identify insertion of the first portion of the electrochemical test strip into the test strip port;
apply a drive signal to the capacitive sensor after the insertion;
measure a first response to the drive signal from the capacitive sensor corresponding to a first level of capacitance in the capacitive sensor;
identify dosing of a fluid sample on a second portion of the electrochemical test strip that is outside of the analyte test meter after the measurement of the first response;
apply the drive signal to the capacitive sensor after the identification of the dosing;
measure a second response to the drive signal from the capacitive sensor corresponding to a second level of capacitance in the capacitive sensor; and
detect contact between a body of a user and at least one electrode in the electrochemical test strip in the second portion of the electrochemical test strip in response to a difference between the first response and the second response exceeding a predetermined threshold.

2. The analyte test meter of claim 1, the controller being further configured to:
measure the first response from the capacitive sensor corresponding to a first time required for the capacitive sensor to discharge to a predetermined voltage level in response to the drive signal; and measure the second response from the capacitive sensor corresponding to a second time required for the capacitive sensor to discharge to the predetermined voltage level in response to the drive signal.

3. The analyte test meter of claim 1, the capacitive sensor further comprising:
a first conductive plate formed in a printed circuit board (PCB) in the analyte test meter; and
a second conductive plate formed from at least one contact in the test strip port in the analyte test meter, the at least one contact being configured to establish an electrical connection to the at least one electrode in the electrochemical test strip.

4. The analyte test meter of claim 3 further comprising:
a resistor connected to the first conductive plate and the second conductive plate to form a resistor-capacitor (RC) circuit.

5. The analyte test meter of claim 1, the capacitive sensor further comprising:
a mutual capacitive sensor.

6. The analyte test meter of claim 1 further comprising:
an output device; and
the controller being operatively connected to the output device and further configured to:
generate an output request for the user to release contact with the electrochemical test strip in response to the detection of the contact between the body of the user and the at least one electrode in the electrochemical test strip.

7. The analyte test meter of claim 6 the controller being further configured to:
detect contact between the body of the user and the at least one electrode in the electrochemical test strip in the second portion of the electrochemical test strip continuously over time in response to the difference between the first response and the second response continuing to exceed the predetermined threshold; and
generate an output request for the user to remove the electrochemical test strip and to test again with a different electrochemical test strip in response to a time of the detection of contact exceeding a predetermined maximum time threshold after the identification of the dosing of the fluid sample.

8. The analyte test meter of claim 1, wherein the controller applies a pulsed direct current (DC) drive signal to the capacitive sensor.

9. The analyte test meter of claim 1, the controller being further configured to:
detect non-contact between the body of the user and the at least one electrode in the electrochemical test strip in the second portion of the electrochemical test strip in response to the difference between the first response and the second response being less than the predetermined threshold; and
apply at least one AC signal, at least one DC signal, or a sequence of AC and DC signals to the electrodes in the electrochemical test strip to detect a level of an analyte in the fluid sample only in response to the detection of non-contact.

10. The analyte test meter of claim 9, the controller being further configured to:
deactivate the drive signal to the capacitive sensor in response to detection that the body of the user is removed from contact from the at least one electrode in the second portion of the electrochemical test strip after the detection that the fluid sample has been applied to the second portion of the electrochemical test strip.

11. The analyte test meter of claim 9, wherein the controller detects glucose in a blood sample applied to the second portion of the electrochemical test strip.

12. A method of operating an analyte test meter comprising:
   identifying, with a controller in the analyte test meter, insertion of the first portion of the electrochemical test strip into a test strip port in the analyte test meter;
   applying, with the controller, a drive signal to a capacitive sensor in the analyte test meter after the insertion;
   measuring, with the controller, a first response to the drive signal from the capacitive sensor corresponding to a first level of capacitance in the capacitive sensor;
   identifying, with the controller, dosing of a fluid sample on a second portion of the electrochemical test strip that is outside of the analyte test meter after the measurement of the first response;
   applying with the controller, the drive signal to the capacitive sensor after the identification of the dosing;
   measuring, with the controller, a second response to the drive signal from the capacitive sensor corresponding to a second level of capacitance in the capacitive sensor; and
   detecting, with the controller, contact between a body of a user and at least one electrode in the electrochemical test strip in the second portion of the electrochemical test strip in response to a difference between the first response and the second response exceeding a predetermined threshold.

13. The method of claim 12 further comprising:
   measuring, with the controller, the first response from the capacitive sensor corresponding to a first time required for the capacitive sensor to discharge to a predetermined voltage level in response to the drive signal; and
   measuring, with the controller, the second response from the capacitive sensor corresponding to a second time required for the capacitive sensor to discharge to the predetermined voltage level in response to the drive signal.

14. The method of claim 12, the applying of the drive signal further comprising:
   applying, with the controller, a pulsed direct current (DC) drive signal to the capacitive sensor.

15. The method of claim 12 further comprising:
   generating, with the controller and an output device in the analyte test meter, an output request for the user to release contact with the electrochemical test strip in response to the detection of the contact between the body of the user and the at least one electrode in the electrochemical test strip.

16. The method of claim 15 further comprising:
   detecting, with the controller, contact between the body of the user and the at least one electrode in the electrochemical test strip in the second portion of the electrochemical test strip continuously over time in response to the difference between the first response and the second response continuing to exceed the predetermined threshold; and
   generating, with the controller and the output device, an output request for the user to remove the electrochemical test strip and to test again with a different electrochemical test strip in response to a time of the detection of contact exceeding a predetermined maximum time threshold after the identification of the dosing of the fluid sample.

17. The method of claim 12 further comprising:
   detecting, with the controller, non-contact between the body of the user and the at least one electrode in the electrochemical test strip in the second portion of the electrochemical test strip in response to the difference between the first response and the second response being less than the predetermined threshold; and
   applying, with the controller, at least one AC signal, at least one DC signal, or a sequence of AC and DC signals to the electrodes in the electrochemical test strip to detect a level of an analyte in the fluid sample only in response to the detection of non-contact.

18. The method of claim 17 further comprising:
   deactivating, with the controller, the drive signal to the capacitive sensor in response to detection that the body of the user is removed from contact from the at least one electrode in the second portion of the electrochemical test strip after the detection that the fluid sample has been applied to the second portion of the electrochemical test strip.

19. The method of claim 15, wherein the controller detects glucose in a blood sample applied to the second portion of the electrochemical test strip.

* * * * *